(12) United States Patent
Ohi

(10) Patent No.: US 10,247,835 B1
(45) Date of Patent: Apr. 2, 2019

(54) RADIATION TOMOGRAPHY APPARATUS

(71) Applicant: Shimadzu Corporation, Kyoto (JP)

(72) Inventor: Junichi Ohi, Kyoto (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 16/084,276

(22) PCT Filed: Jan. 16, 2017

(86) PCT No.: PCT/JP2017/001221
§ 371 (c)(1),
(2) Date: Sep. 12, 2018

(87) PCT Pub. No.: WO2017/199464
PCT Pub. Date: Nov. 23, 2017

(30) Foreign Application Priority Data

May 19, 2016 (JP) .................. 2016-100338

(51) Int. Cl.
| | | |
|---|---|---|
| G01T 1/29 | (2006.01) |
| G01T 1/161 | (2006.01) |
| G01T 1/164 | (2006.01) |
| A61B 6/03 | (2006.01) |
| A61B 6/00 | (2006.01) |
| G01T 1/202 | (2006.01) |

(52) U.S. Cl.
CPC .......... *G01T 1/2985* (2013.01); *A61B 6/037* (2013.01); *A61B 6/4429* (2013.01); *G01T 1/161* (2013.01); *G01T 1/164* (2013.01); *G01T 1/202* (2013.01)

(58) Field of Classification Search
CPC ....... A61B 6/037; A61B 6/4429; G01T 1/161; G01T 1/164; G01T 1/202; G01T 1/2985
See application file for complete search history.

(56) References Cited

U.S. PATENT DOCUMENTS

2003/0072416 A1* 4/2003 Rasche .................. A61B 6/032
378/197

OTHER PUBLICATIONS

Y. Yoshiyuki, et al., "Development of a dual-head mobile DOI-TOF PET system having multi-modality compatibility," in Conf. Rec. IEEE NSS/MIC, 2014, M11-69., 3 pgs.
International Search Report dated Apr. 11, 2017 of corresponding application No. PCT/JP2017/001221; 4 pgs.

* cited by examiner

*Primary Examiner* — Mark R Gaworecki
(74) *Attorney, Agent, or Firm* — Maier & Maier, PLLC

(57) ABSTRACT

A detector ring has a first unit and a second unit that are rotatably movable and an auxiliary unit movable in a central axis direction. The auxiliary unit is moved in the central axis direction relative to the units. The detector ring forms into a C shape to form a clearance. Subsequently, the first unit and the second unit are rotatably moved to move the clearance of the detector ring to a position distant from a support member. A patient can be introduced from the clearance. The detector ring is returned to an annular shape in the reverse sequence of the above one with the patient introduced. A annihilation radiation pairs can be detected from all directions to take a tomographic image, and a functional image with higher image quality than that of a conventional configuration can be obtained.

9 Claims, 11 Drawing Sheets

RADIATION TOMOGRAPHY APPARATUS

FIELD

The present invention relates to a radiation tomography apparatus that detects annihilation radiation pairs emitted from a patient to image radioactive agent distribution within the patient and, in particular, to a radiation tomography apparatus used in combination with another imaging apparatus.

BACKGROUND

Radiation tomography apparatuses that image the distribution of a radioactive agent are deployed in medical institutions. The following describes a specific configuration of such a radiation tomography apparatus. A conventional radiation tomography apparatus includes a detector ring including radiation detectors annularly arranged and detecting radiations. This detector ring detects a pair of radiations that are emitted from a radioactive agent within a patient and are opposite in direction to each other (an annihilation radiation pair). Such an apparatus is called a positron emission tomography (PET) apparatus.

FIG. 17 illustrates a typical PET apparatus. The PET apparatus is of the stationary type fixed to a floor of a inspection room, and a patient is introduced from an opening provided in the PET apparatus. An image obtained by this PET apparatus means the distribution of the radioactive agent within the patient. Consequently, the distribution of a highly-concentrated radioactive agent on this image would not always definitely indicate which organ of the patient.

Given these circumstances, as illustrated in FIG. 17, an image imaging apparatus including both the PET apparatus and a CT apparatus has been devised and widely used. The CT apparatus of this imaging apparatus gives a morphological image showing the internal structure of the patient, whereas the PET apparatus gives a functional image showing the distribution of the radioactive agent. When morphological image and the functional image are displayed in a superimposed manner, a viewer of the images can tell which part of the patient the radioactive agent has been distributed.

The following describes the reason why the PET apparatus and the CT apparatus are arranged close to each other. Suppose that the PET apparatus and the CT apparatus are prepared in different inspection rooms, for example. In such a configuration, a morphological image is first taken with the CT apparatus, then the patient is moved to another room, and a functional image is taken with the PET apparatus. In such as a configuration, the morphological image and the functional image cannot be precisely superimposed on one another. This is because the postures of the patient when imaged by the respective apparatuses are different from each other. To reduce such image discrepancy, the PET apparatus and the CT apparatus are provided close to each other. By doing so, once the patient is placed on a patient couchpatient couch, there is no need to take down the patient from the patient couchpatient couch until capture of the morphological image and the functional image ends. The apparatus in FIG. 17, allows the CT and PET apparatuses to finish imaging while the patient maintains the same posture, such that the obtained morphological image and functional image can be precisely superimposed on one another.

However, imaging with the CT apparatus creates a large amount of exposure dose and is not suitable for pregnant women, children, and the like, who have high radiosensitivity. Hence, apparatuses gradually in common in recent years are a PET/MRI apparatus whose CT apparatus illustrated in FIG. 17 is replaced with an MRI apparatus, and a completely integral type PET/MRI apparatus in which detectors of a PET apparatus are contained within an imaging field of view of an MRI apparatus. However, the PET/MRI apparatus is large-scale in configuration, and the price of the apparatus itself tends to be extraordinarily high. Some medical institutions already having an MRI apparatus may desire a PET apparatus that can be placed by the side of the MRI apparatus. In view of such a need, a mobile type PET apparatus as illustrated in FIG. 18 has been devised in recent years. In this mobile type PET apparatus, when a patient is placed on a patient couch included in the MRI apparatus, a functional image can be taken without moving the patient from this patient couch (see NON-PATENT DOCUMENT 1, for example).

The patient couch included in the MRI apparatus has a long, narrow shape to fit the patient. The patient couch is movable in a longitudinal direction (the body axis direction of the patient placed on the patient couch). This is because the patient is required to be introduced into a gantry of the MRI apparatus. The mobile type PET apparatus is brought close to and separated from the patient couch in the lateral direction of the patient couch (the body side direction of the patient placed on the patient couch) as indicated by the arrow in FIG. 18. When imaging is performed with the PET apparatus, the patient and the patient couch are required to be introduced inside the detector ring. In a conventional configuration, for the purpose of introducing the detector ring from the body side direction of the patient, the detector ring is provided with a clearance A. This clearance A makes the detector ring form into a C shape.

FIG. 19 illustrates how the patient is actually introduced inside the detector ring. The detector ring is provided with the clearance A, whereby the patient and the patient couch are introduced into the center of the detector ring without being interfered with the detector ring.

FIG. 20 illustrates the transformation of the detector ring performed before starting PET imaging. In other words, the detector ring immediately after the introduction of the patient illustrated on the left side in FIG. 20 is transformed so that the transformed detector ring vertically sandwiches a patient M therebetween as illustrated on the right side in FIG. 20. The detector ring of the mobile type PET apparatus forms a C shape by combining two arc members with each other. These members can rotate and move about the central point of the detector ring. With this movement, the clearance A appearing on the right side of the detector ring is divided into right and left.

Essentially, the detector ring is desirably annularly shaped. If it is not so shaped, annihilation radiation pairs are unevenly detected, making it difficult for a clear functional image to be taken. However, the clearance A has to be provided to the mobile type PET apparatus because a path is required to introduce the patient through the path. Consequently, in the conventional configuration, after the patient is introduced, the detector ring is transformed to divide the clearance A, whereby the influence of the clearance A appearing in the functional image is ingeniously reduced to a minimum.

NON-PATENT DOCUMENT

NON-PATENT DOCUMENT 1: Y. Yoshiyuki, et al., "Development of a dual-head mobile DOI-TOF PET system having multi-modality compatibility," in Conf. Rec. IEEE NSS/MIC, 2014, M11-69.

SUMMARY

The conventional configuration has the following problem.

In other words, the conventional configuration does not completely reduce image degradation caused by providing the clearance in the detector ring.

Although the conventional configuration reduces image degradation caused by the provided clearance A, image degradation cannot yet be completely prevented. To achieve clearer image quality, PET imaging is desirably performed using an annularly shaped detector ring.

However, the mobile type PET apparatus requires the clearance A to introduce the patient. Consequently, it is also difficult not to provide the clearance A.

The present invention has been made in view of such circumstances, and an object thereof is to provide a radiation tomography apparatus that can generate a functional image with good image quality by providing a detector ring that is annularly shaped and can introduce the patient from a direction orthogonal to a central axis.

To solve the problems described above, the present invention has the following configuration.

In other words, the radiation tomography apparatus according to the present invention includes: a detector ring including (i) a first unit including radiation detectors arranged in an arc and detecting radiations, (ii) a second unit including the radiation detectors arranged in an arc, and (iii) an auxiliary unit including the radiation detectors arranged in an arc, such that the radiation detectors included in the first unit, the second unit, and the auxiliary unit are arranged annularly; a support member that supports the detector ring and is provided close to the auxiliary unit among the units; an auxiliary unit mover that moves the auxiliary unit in a central axis direction of the detector ring relative to the first unit and the second unit; a first unit rotator that rotatably moves the first unit about the central axis; and a second unit rotator that rotatably moves the second unit about the central axis.

[Advantages] The present invention can provide a radiation tomography apparatus that can generate a functional image with good image quality. In other words, in the configuration of the present invention, the annular-shaped detector ring has the first unit and the second unit that are rotatably movable and the auxiliary unit movable in the central axis direction. The auxiliary unit is moved in the central axis direction relative to the units, whereby the detector ring forms into a C shape to form a clearance.

However, the support member supporting the auxiliary unit is positioned near this clearance. Hence, in the present invention, the first unit and the second unit are rotatably moved additionally to move the clearance of the detector ring to a position distant from the support member. By doing so, a patient can be introduced from a direction orthogonal to the central axis of the detector ring without interference from the support member. The detector ring is restored to the annular shape in the reverse sequence of the above one with the patient introduced, whereby annihilation radiation pairs can be detected from all directions to take a tomographic image, and a functional image with higher image quality than that of a conventional configuration can be obtained.

In the present invention, all the members included in the detector ring are supported on the single support member. With this configuration, the positional relationship among the units included in the detector ring can be reliably maintained constant. In this regard, in a configuration in which the units are supported on separate support members, when the positional relationship among the support members changes, the shape of the detector ring also changes. The present invention is free from such an inconvenience.

In the radiation tomography apparatus described above, the first unit rotator may rotate the first unit and the second unit rotator may rotate the second unit to bring the first unit and the second unit close to the support member, so that end parts of the first unit and the second unit, adjacent to each other before the rotations, may be separated from each other, and a clearance may be generated between the first unit and the second unit such that, through the clearance, a patient may be introduced inside the detector ring from a direction orthogonal to the central axis.

In the radiation tomography apparatus described above, the first unit rotator may rotate the first unit and the second unit rotator may rotate the second unit to separate the first unit and the second unit from the support member, so that end parts of the first unit and the second unit, adjacent to each other before the rotations, may be separated from each other, and a clearance may be generated between the first unit and the second unit such that, through the clearance, the auxiliary unit may be introduced from a direction in which the central axis extends.

[Advantages] The configuration described above can reliably achieve the configuration of the present invention.

The radiation tomography apparatus described above may desirably include a first arc guide fixing the first unit and a second arc guide fixing the second unit, in which the first unit rotator rotates the first guide to perform rotational movement of the first unit, and the second unit rotator rotates the second guide to perform rotational movement of the second unit.

[Advantages] The configuration described above can provide an apparatus that can reliably rotate the units.

The radiation tomography apparatus described above may desirably include an arc guide supporting the first unit and the second unit, in which the first unit rotator moves the first unit relative to the guide to perform rotational movement of the first unit, and the second unit rotator moves the second unit relative to the guide to perform rotational movement of the second unit.

[Advantages] The configuration described above can make the configuration of the apparatus simpler than the configuration including the first guide and the second guide.

The radiation tomography apparatus described above may desirably include a vehicle moving the detector ring in a direction orthogonal to the central axis.

[Action and Effect] The configuration described above allows the entire apparatus to be moved close to the patient mounted on a patient couch from the body side direction of the patient.

The radiation tomography apparatus described above may desirably include a support member elevator that raises and lowers the support member to raise and lower the detector ring.

[Advantages] The configuration described above can align the patient and the detector ring with each other with the positional relationship reliably maintained among the members included in the detector ring.

The radiation tomography apparatus described above may desirably be arranged in an MRI apparatus.

The radiation tomography apparatus described above may desirably be arranged in a CT apparatus.

[Advantages] The present invention can be used in combination with the MRI apparatus or the CT apparatus.

The present invention can provide a radiation tomography apparatus that can generate a functional image with good image quality. In other words, in the configuration of the present invention, an annular-shaped detector ring has a first unit and a second unit that are rotatably movable and an auxiliary unit movable in a central axis direction. The auxiliary unit is moved in the central axis direction of the detector ring relative to the units, whereby the detector ring forms into a C shape to form a clearance. Subsequently, the first unit and the second unit are rotatably moved to move a clearance of the detector ring to a position distant from a support member, whereby a patient can be introduced from the clearance. The detector ring is restored to an annular shape in the reverse sequence of the above one with the patient introduced, whereby annihilation radiation pairs can be detected from all directions to take a tomographic image, and a functional image with higher image quality than that of a conventional configuration can be obtained.

DETAILED DESCRIPTION

The following describes embodiments of the present invention with reference to an example. A radiation tomography apparatus according to the present invention is a PET apparatus that injects a compound labeled with a positron emission type radioactive isotope into a patient and detects annihilation radiation pairs to image the distribution of the compound within the body of the patient. The following example describes a PET apparatus used in combination with an MRI apparatus.

[Example 1]

Figure 1:
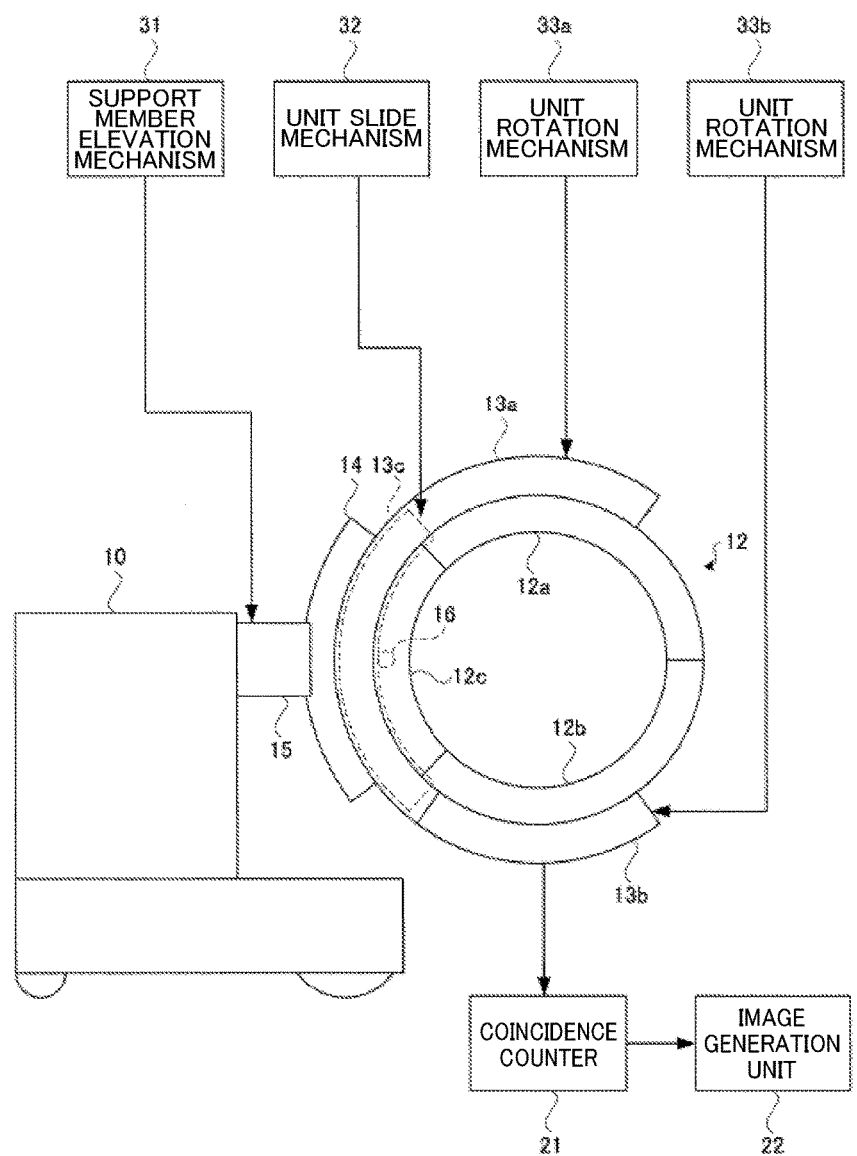
FIG. 1 is a functional block diagram illustrating an entire configuration of a radiation tomography apparatus according to Example 1.
Figure 2:
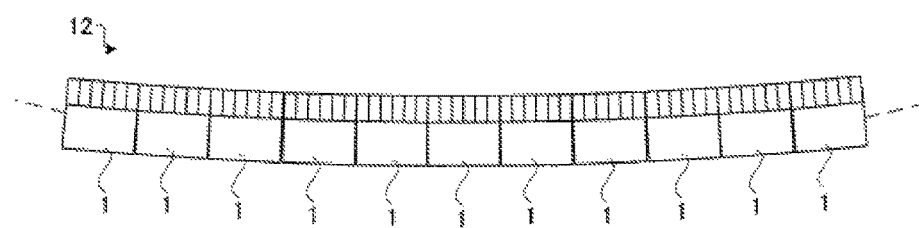
FIG. 2 is a schematic diagram illustrating a detector ring according to Example 1.

FIG. 1 illustrates units included in the radiation tomography apparatus according to the present invention. The radiation tomography apparatus according to the present invention includes a vehicle 10 having wheels and a detector ring 12 installed on the vehicle 10. As illustrated in FIG. 2, the detector ring 12 includes radiation detectors 1 detecting radiations arranged in an arc. A support member 15 supports one end of the detector ring 12 to support the entire detector ring 12. Specifically, the support member 15 supports each of a first guide 13a, a second guide 13b, and an auxiliary guide 13c described below to support the detector ring 12. All loads of the detector ring 12 and the guides 13a, 13b, and 13c are supported on the single support member 15. The vehicle 10 moves the detector ring 12 in a direction orthogonal to a central axis c.

Figure 3:
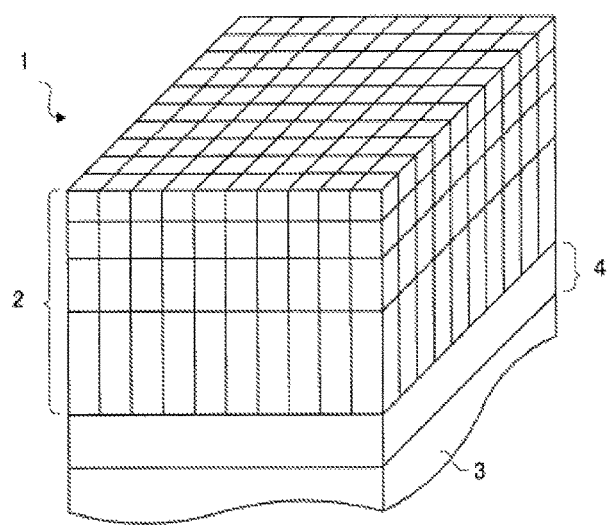
FIG. 3 is a perspective view illustrating a detector according to Example 1.

FIG. 3 illustrates a configuration of the radiation detector 1. The radiation detector 1 includes a scintillator 2 including scintillator crystals that convert radiations (gamma rays) into fluorescence arranged in a three-dimensional manner in three, or longitudinal, lateral, and height, directions. The scintillator 2 is optically coupled to a light guide 4 that passes the fluorescence, and the light guide 4 is optically coupled to an optical detector 3 detecting fluorescence. Consequently, the light guide 4 is arranged at a position interposed between the scintillator 2 and the optical detector 3. When the fluorescence is generated in the scintillator 2, the optical detector 3 can determine which scintillator crystal generates the fluorescence.

To a coincidence counter 21 (see FIG. 1), a detection signal output from the detector ring 12 is sent. Two gamma rays that have coincidentally entered the detector ring 12 are a radiation pair caused by a radioactive agent within the patient. The coincidence counter 21 counts how many radiation pairs have been detected for each combination of two scintillator crystals among the scintillator crystals included in the detector ring 12. For the determination of the coincidence of the detection signal by the coincidence counter 21, time information imparted to the detection signal by a clock is used. The detection signal sent to the coincidence counter 21 indicates a result of detecting radiations caused by the radioactive agent administered to a patient M. The detection signal output by the coincidence counter 21 is a result of detecting the radiation pair emitted from any given part of the imaging field of view of the detector ring 12 and is a result of measuring the radiation pair throughout the entire detector ring 12.

The coincidence counter 21 sends data indicating the result of counting to an image generation unit 22. Based on the sent data, the image generation unit 22 images the distribution of the radioactive agent in the imaging fields of view positioned inside the detector ring 12, and generates a tomographic image.

<Configuration of Support Member Elevation Mechanism 31>

Figure 4:
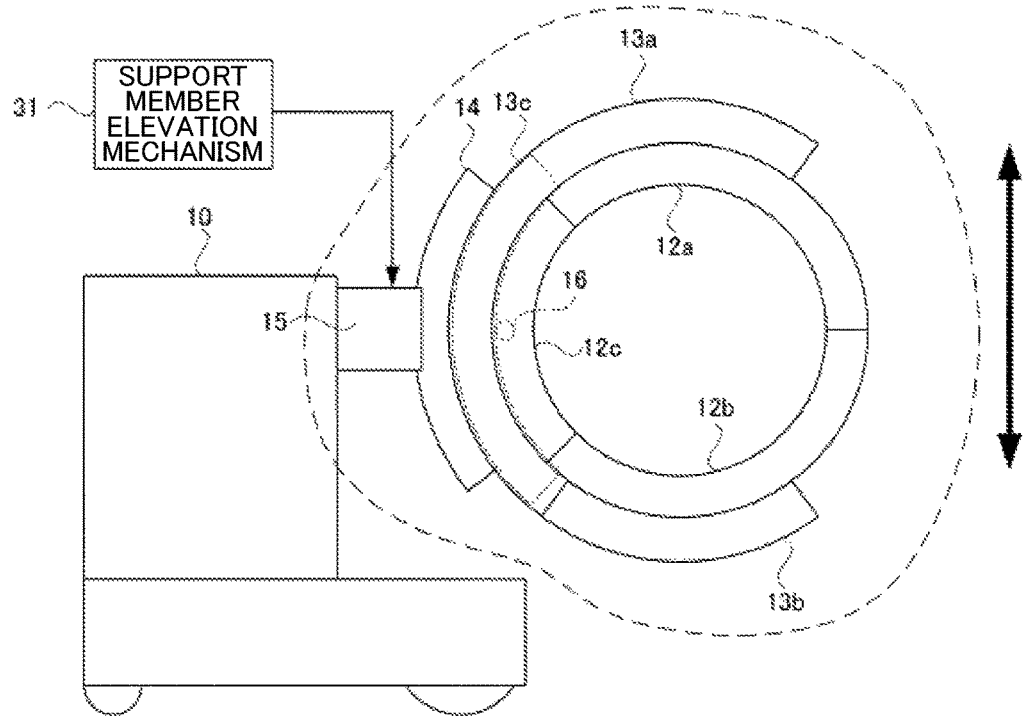
FIG. 4 is a schematic diagram illustrating a support member elevation mechanism according to Example 1.

A support member elevation mechanism 31 is provided in the vehicle 10 and raises and lowers the support member 15 relative to the vehicle 10. When the support member 15 is raised and lowered by the support member elevation mechanism 31, as illustrated in FIG. 4, the detector ring 12, the guides 13a, 13b, and 13c, and a rotation base 14 and a slide rail 16 described below follow the support member 15 to be raised and lowered with their mutual positional relationship maintained. The support member elevation mechanism 31 raises and lowers the support member 15 to raise and lower the detector ring 12. The support member elevation mechanism 31 corresponds to a support member elevator of the present invention.

<Division of Detector Ring 12>

The detector ring 12 of the present invention includes three members annularly arranged and capable of mutually changing their positional relationship. In other words, the detector ring 12 includes a first unit 12a, a second unit 12b, and an auxiliary unit 12c formed in an arc and arranged to form a circle. The auxiliary unit 12c among them is positioned closest to the support member 15. The first unit 12a, the second unit 12b, and the auxiliary unit 12c include radiation detectors 1 arranged in an arc and detecting radiations. The first unit 12a, the second unit 12b, and the auxiliary unit 12c are arranged in an arc to form the detector ring 12 in which the radiation detectors 1 are annularly arranged. The support member 15 supports the detector ring 12 and is provided adjacent to the auxiliary unit 12c among the units 12a, 12b, and 12c.

<Relationship Between Units and Guides>

Figure 5:
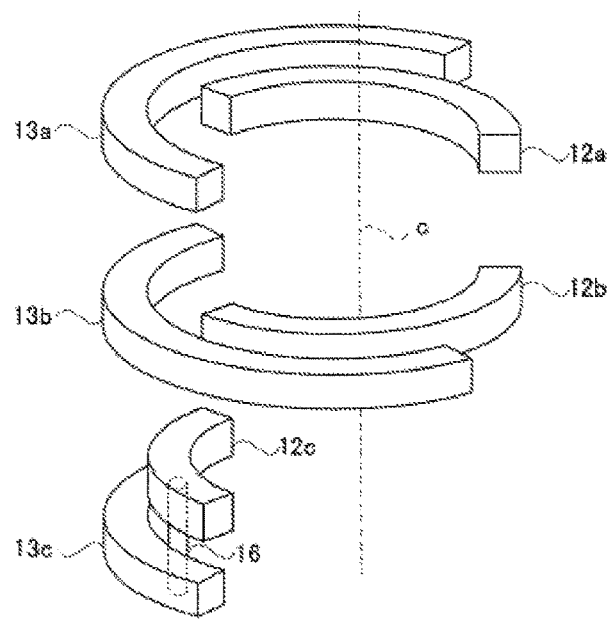
FIG. 5 is an exploded perspective view illustrating units included in the detector ring according to Example 1.

The units 12a, 12b, and 12c included in the detector ring 12 are supported on the respective guides 13a, 13b, and 13c in order to move the respective units. The following describes this configuration. FIG. 5 is an exploded perspective view of the detector ring 12 and illustrates the respective guides similarly. The first arc guide 13a is fixed to the first unit 12a. The first guide 13a is offset toward a central axis c of the detector ring 12 relative to the first unit 12a. In FIG. 5, the first guide 13a is offset upward relative to the first unit 12a.

The second arc guide 13b is fixed to the second unit 12b. The second guide 13b is offset toward the central axis c of the detector ring 12 relative to the second unit 12b. In FIG. 5, the second guide 13b is offset downward relative to the second unit 12b.

The first guide 13a and the second guide 13b thus are offset from each other in different directions relative to the detector ring 12. Being thus configured, the first guide 13a and the second guide 13b do not interfere with each other. In other words, the guides 13a and 13b are in a different position form each other in the central axis c direction, and even when the first guide 13a and the second guide 13b are rotated about the central axis c, the guides 13a and 13b do not collide with each other.

The auxiliary unit 12c is provided with an arc auxiliary guide 13c. It should be noted that this auxiliary guide 13c is not fixed to the auxiliary unit 12c. The slide rail 16 extending parallel to the central axis is fixed to the auxiliary unit 12c. The auxiliary guide 13c supports this slide rail 16 in a movable manner in the central axis direction.

Figure 6:
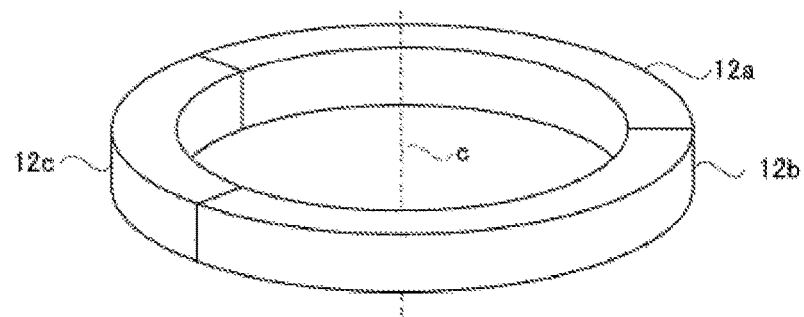
FIG. 6 is a perspective view illustrating the units included in the detector ring according to Example 1.

FIG. 5, because of being an exploded perspective view, illustrates the units 12a, 12b, and 12c so that the units 12a, 12b, and 12c are in a different position in the central axis c direction. However, the units 12a, 12b, and 12c are actually in the same position relative to the central axis c direction and form one detector ring 12 as illustrated in FIG. 6. In FIG. 6, the guides 13a, 13b, and 13c are omitted.

<About Unit Slide Mechanism 32>

Figure 7:
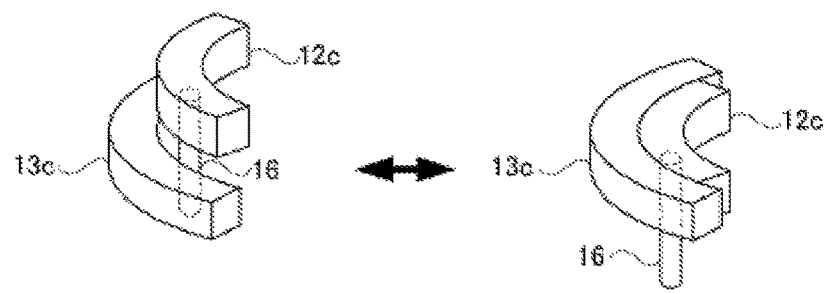
FIG. 7 is a schematic diagram illustrating the movement of an auxiliary unit according to Example 1.
Figure 8:
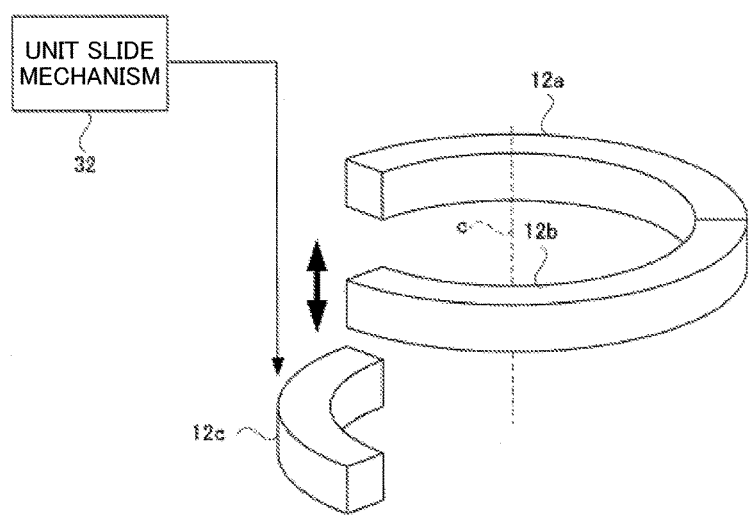
FIG. 8 is a schematic diagram illustrating a unit slide mechanism according to Example 1.

FIG. 7 illustrates how the auxiliary unit 12c moves in the central axis direction relative to the auxiliary guide 13c. With this motion, as illustrated in FIG. 8, the auxiliary unit 12c can move in the central axis c direction relative to the units 12a and 12b. With this movement, the detector ring 12 changes from the annular shape formed with the units 12a, 12b, and 12c to a C shape formed with the units 12a and 12b because the auxiliary unit 12c moves in the central axis c direction. This motion of the auxiliary unit 12c is performed by a unit slide mechanism 32. In other words, the auxiliary guide 13c is fixed to the support member 15, and the auxiliary unit 12c moves relative to the auxiliary guide 13c and thereby moves relative to the support member 15 and the units 12a and 12b supported thereby. The auxiliary guide 13c and the slide rail 16 are included in the members included in the unit slide mechanism 32. The unit slide mechanism 32. moves the auxiliary unit 12c in the central axis c direction of the detector ring 12 and moves the auxiliary unit 12c relative to the units 12a and 12b. The unit slide mechanism 32 corresponds to an auxiliary unit mover of the present invention.

<Unit Rotation Mechanisms 33a and 33b>

When the auxiliary unit 12c forms the detector ring 12 as in FIG. 6, the units 12a and 12b cannot be rotated about the central axis c. However, when the auxiliary unit 12c moves relative to the units 12a and 12b to form a broken ring in which part of the detector ring 12 is broken as in FIG. 8, the units 12a and 12b can rotate. In fact, the apparatus according to the present invention can rotate the units 12a and 12b. The following describes this point. A unit rotation mechanism 33a corresponds to a first unit rotator of the present invention.

Figure 9:
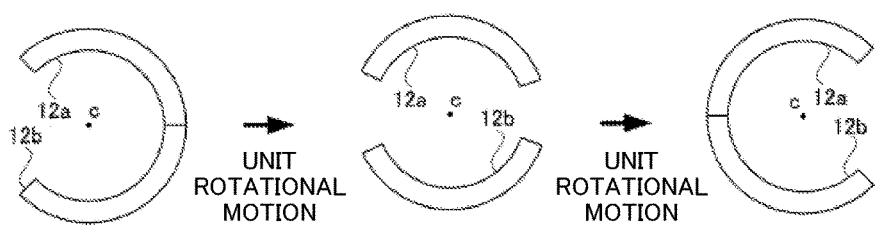
FIG. 9 is a schematic diagram illustrating unit rotational motion according to Example 1.

The left side in FIG. 9 illustrates a state in which the auxiliary unit 12c has moved relative to the units 12a and 12b. At this moment, it is shown that a clearance has been produced on the left side of the units 12a and 12b. The units 12a and 12b can rotate about the central axis c while following the locus of an arc. With this rotation, the units 12a and 12b are positioned on a certain circle even when they are rotated. The center in FIG. 9 illustrates a result obtained by synchronously rotating the units 12a and 12b. The first unit 12a at this moment is positioned in an upper part of the detector ring 12, whereas the second unit 12b is positioned in a lower part of the detector ring 12. The right side in FIG. 9 illustrates a state in which the units 12a and 12b have been moved to the left side of the detector ring 12. In this state, the units 12a and 12b are in contact with each other on the left side, producing a clearance on the right side of the units 12a and 12b.

In other words, after having moved relative to the units 12a and 12b, the unit rotation mechanism 33a rotatably moves the first unit 12a about the central axis, whereas after having moved relative to the units 12a and 12b, a unit rotation mechanism 33b rotatably moves the second unit 12b about the central axis. The unit rotation mechanisms 33b corresponds to a second unit rotator of the present invention.

Such motions of the units 12a and 12b are performed by the respective guides 13a and 13b. In other words, the guides 13a and 13b are supported on the arc rotation base 14. The rotation base 14 is a guide when the first guide 13a rotatably moves, and the first guide 13a follows the locus of an arc in accordance with the shape of the rotation base 14. The center of this rotation overlaps with the central axis c of the detector ring 12. In other words, the first guide 13a is supported on the rotation base 14 in a movable manner. The first unit 12a follows this first guide 13a to rotatably move.

These circumstances hold true for the second guide 13b. In other words, the rotation base 14 is a guide when the second guide 13b rotatably moves, and the second guide 13b follows the locus of an arc in accordance with the shape of the rotation base 14. The center of this rotation overlaps with the central axis c of the detector ring 12. In other words, the second guide 13b is supported on the rotation base 14 in a movable manner. The second unit 12b follows this second guide 13b to rotatably move.

In other words, the apparatus according to the present invention includes the first arc guide 13a fixing the first unit 12a and the second arc guide 13b fixing the second unit 12b. The unit rotation mechanism 33a rotates the first guide 13a to perform rotational movement of the first unit 12a, whereas the unit rotation mechanism 33b rotates the second guide 13b to perform rotational movement of the second unit 12b.

The rotation base 14 is fixed to the support member 15. Consequently, even when the units 12a and 12b rotate, the rotation base 14 does not move relative to the support member 15.

<Introduction of Patient M>

The following describes a method for introducing the patient M into the apparatus according to Example 1. FIG. 10 again illustrates the detector ring 12 illustrated on the right side in FIG. 9 including the entire apparatus. In the detector ring 12 in this state, the auxiliary unit 12c has moved relative to the units 12a and 12b and is hidden in back of the detector ring 12 in FIG. 10. The first unit 12a and the second unit 12b are adjacent to each other while being close to the support member 15 on the left side of the detector ring 12 and form one C-shaped detector ring 12. On the right side of the detector ring 12 (the side opposite the support member 15), a clearance is produced between the first unit 12a and the second unit 12b. This clearance is not covered with the first guide 13a and the second guide 13b. Consequently, the central axis c of the detector ring 12 is exposed out of this clearance to the outside of the apparatus when viewed from the right side in FIG. 10.

Figure 18:
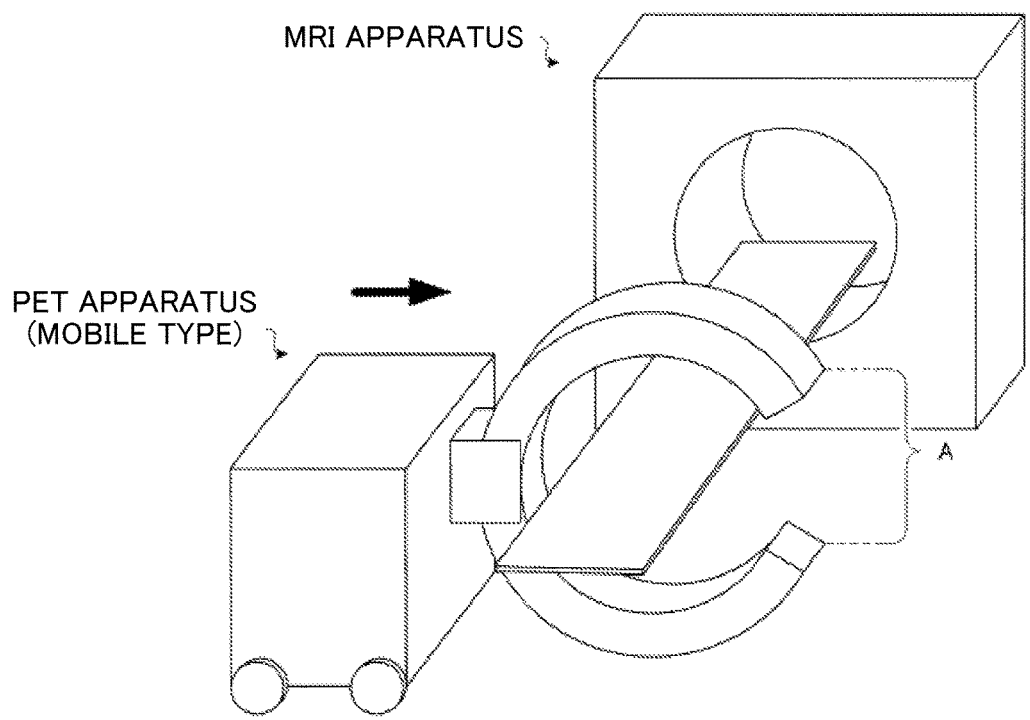
FIG. 18 is a schematic diagram illustrating a mobile type PET apparatus of a conventional configuration.
Figure 19:
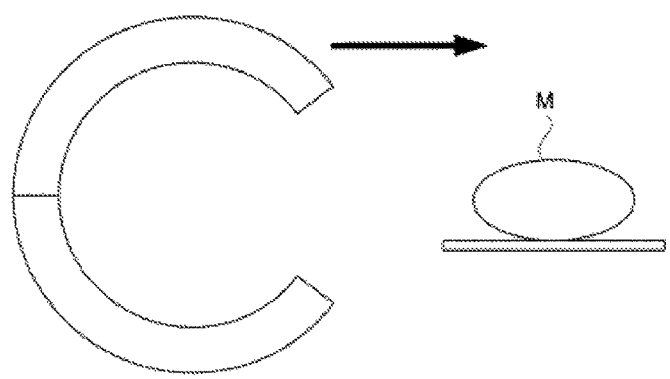
FIG. 19 is a schematic diagram illustrating a method for introducing a patient of a conventional configuration.
Figure 20:
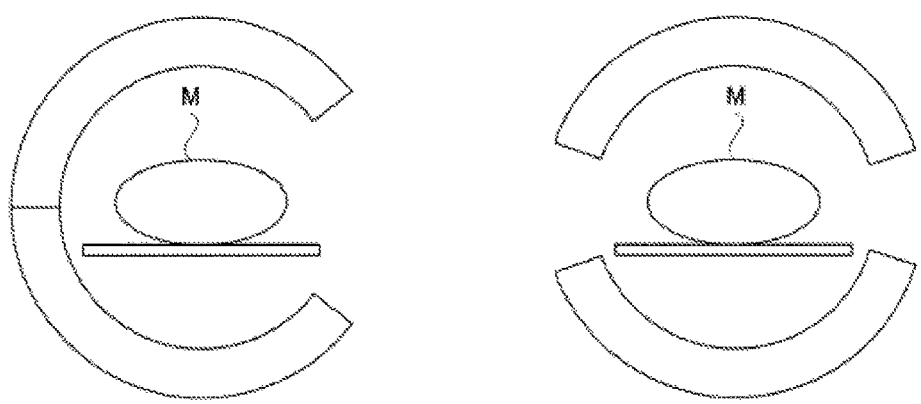
FIG. 20 is a schematic diagram illustrating a method of imaging of a conventional configuration.

The patient M can be introduced into the detector ring 12 from this clearance produced in the detector ring 12. The following describes this point. On the right side in FIG. 10, a patient couch 42 and a base 41 supporting it are drawn. This patient couch 42 is formed in a long, narrow shape extending in a direction passing through the drawing, on which the patient M can be placed. The body axis direction of the patient M on this patient couch 42 overlaps with the direction passing through the drawing. Consequently, the right-and-left direction of FIG. 10 corresponds to the body side direction of the patient M. Although not illustrated in FIG. 10, the patient couch 42 and the base 41 are included in the MRI apparatus. The positional relationship among the MRI apparatus, the patient couch 42, and the radiation tomography apparatus according to the present invention is the same as that in FIG. 18. In other words, the central axis c of the detector ring 12 in FIG. 10 extends in the body axis direction of the patient M.

Figure 10:
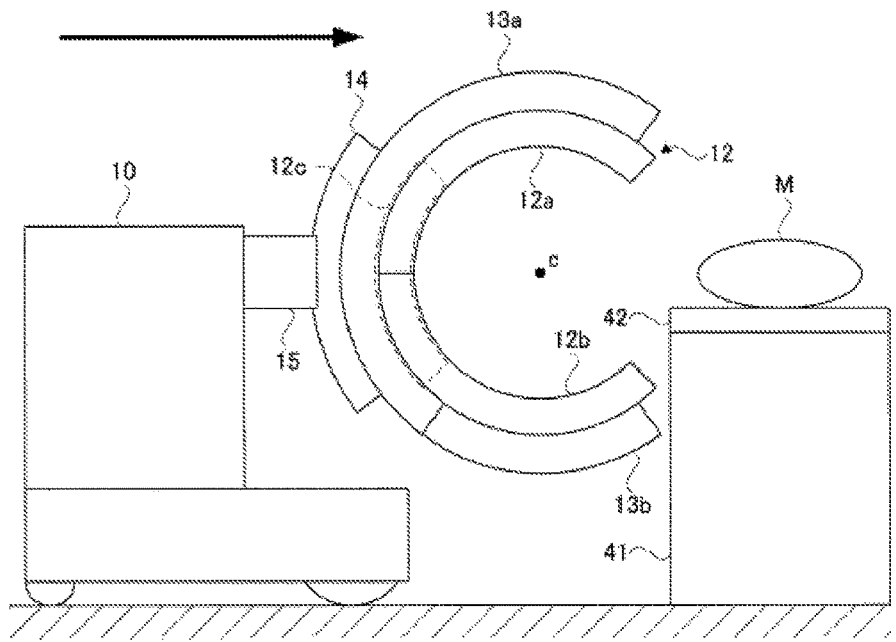
FIG. 10 is a schematic diagram illustrating an operation to introduce a patient according to Example 1.

The radiation tomography apparatus includes the vehicle 10, and the entire apparatus can be moved in the body side direction of the patient M (the right-and-left direction in FIG. 10 perpendicular to the central axis c of the detector ring 12 and the vertical direction). When the apparatus is moved close to the patient M, the patient couch 42 and the patient M positioned outside the apparatus approach the detector ring 12 from the body side direction, pass through the clearance of the detector ring 12, and are introduced inside the detector ring 12. Although the base 41 is drawn as if it collided with the detector ring 12 in FIG. 10, the actual base 41 is positioned on the near side of the detector ring 12, and such a collision will not occur.

Figure 11:
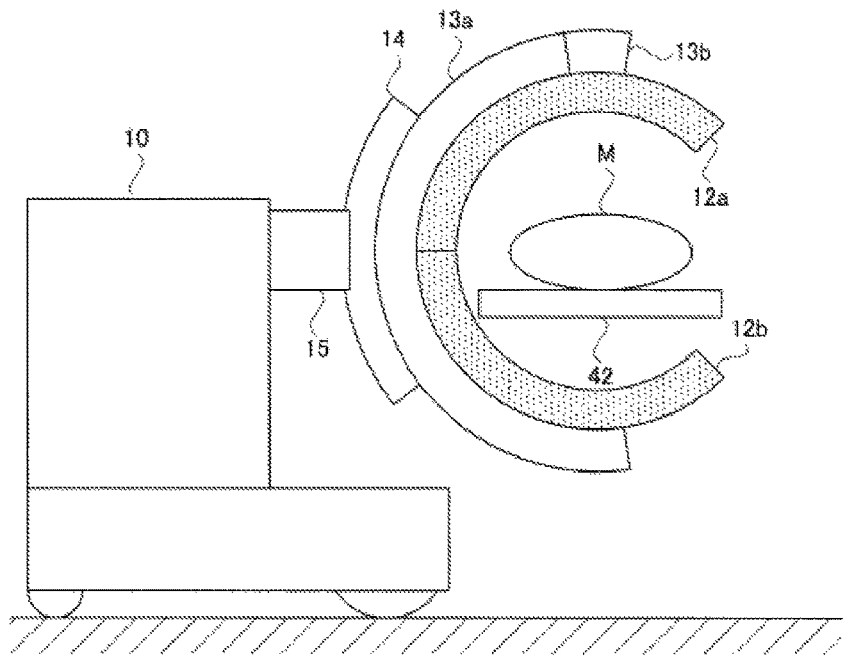
FIG. 11 is a schematic diagram illustrating the operation to introduce the patient according to Example 1.
Figure 12:
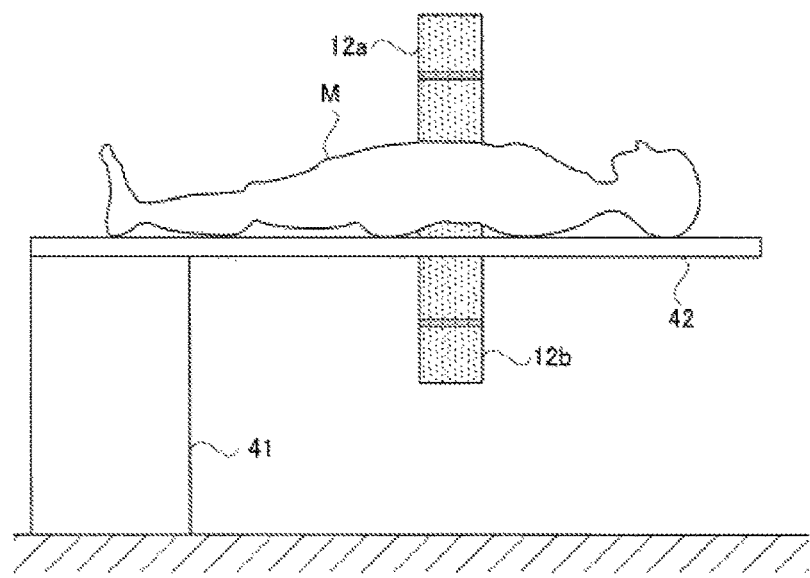
FIG. 12 is a schematic diagram illustrating the operation to introduce the patient according to Example 1.

FIG. 11 illustrates a state in which the patient M has been introduced inside the detector ring 12. At this moment, the central axis c of the detector ring 12 is positioned inside the patient M. Immediately after the patient M has been introduced, the detector ring 12 forms a C shape, which resembles the conventional configuration illustrated in FIG. 18 at first glance. In FIG. 11, the units 12a and 12b included in the detector ring 12 are drawn with emphasis by shading. FIG. 12 illustrates the apparatus in the state in FIG. 11 from a different viewpoint. FIG. 12 shows that the patient M is stationary inside the C-shaped detector ring 12.

In the apparatus according to the present invention, the unit rotation mechanism 33a and the unit rotation mechanism 33b cooperatively work upon the detector ring 12, in which the auxiliary unit 12c has moved relative to the units 12a and 12b, to rotate the units 12a and 12b to the left side (to bring the units 12a and 12b close to the support member 15) (see FIG. 9). With this rotation, end parts of the respective units 12a and 12b adjacent to each other before the rotations are separated from each other, and a clearance is generated between the units 12a and 12b so that, through the clearance, the patient M is introduced inside the detector ring 12.

<Most Characteristic Feature of the Present Invention: Transformation of Detector Ring 12>

Figure 13:
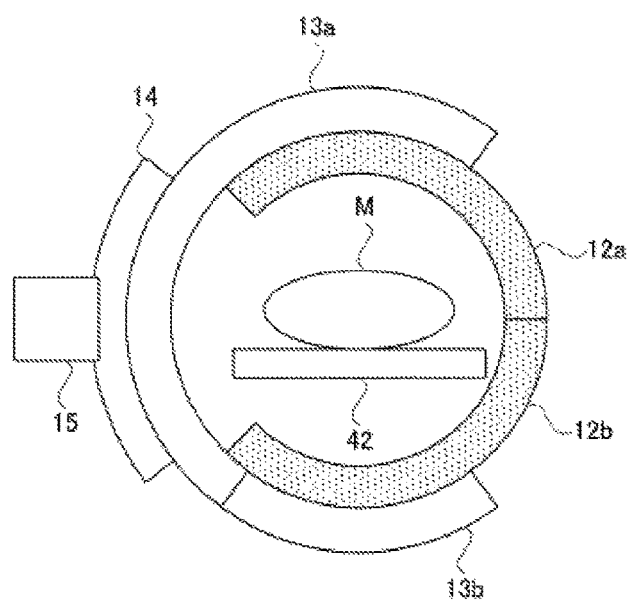
FIG. 13 is a schematic diagram illustrating an operation to transform the detector ring according to Example 1.

The following describes the most characteristic feature of the present invention. In other word, the detector ring 12 according to the present invention can transform from a C shape into an annular shape with the patient M introduced. To perform this transformation, first, the units 12a and 12b are rotatably moved. In other words, operation in the reverse sequence of the illustration in FIG. 9 is performed, whereby the units 12a and 12b are rotated so as to be moved to the right side (separated from the support member 15). Then the clearance positioned on the right side of the detector ring 12 is moved to the left side. FIG. 13 illustrates the detector ring 12 when this rotational motion ends. Such rotational motion is performed by the unit rotation mechanisms 33a and 33b. The clearance that has moved to the left side of the detector ring 12 ensures space just required for the auxiliary unit 12c to enter.

Thus, in the present invention, the unit rotation mechanism 33a and the unit rotation mechanism 33b rotate the respective units 12a and 12b to separate that the respective units 12a and 12b from the support member 15, so that the end parts of the respective units 12a and 12b, adjacent to each other before the rotations, are separated from each other, and a clearance is generated between the units 12a and 12b such that, through the clearance, the auxiliary guide 13c is introduced from a direction in which the central axis c extends.

Figure 14:
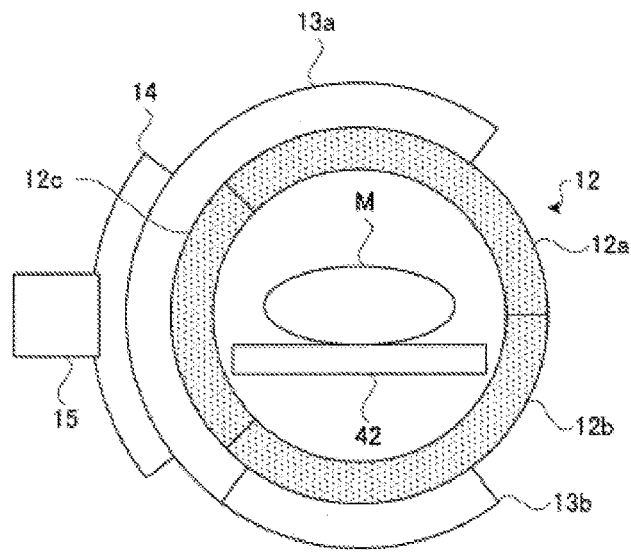
FIG. 14 is a schematic diagram illustrating the operation to transform the detector ring according to Example 1.
Figure 15:
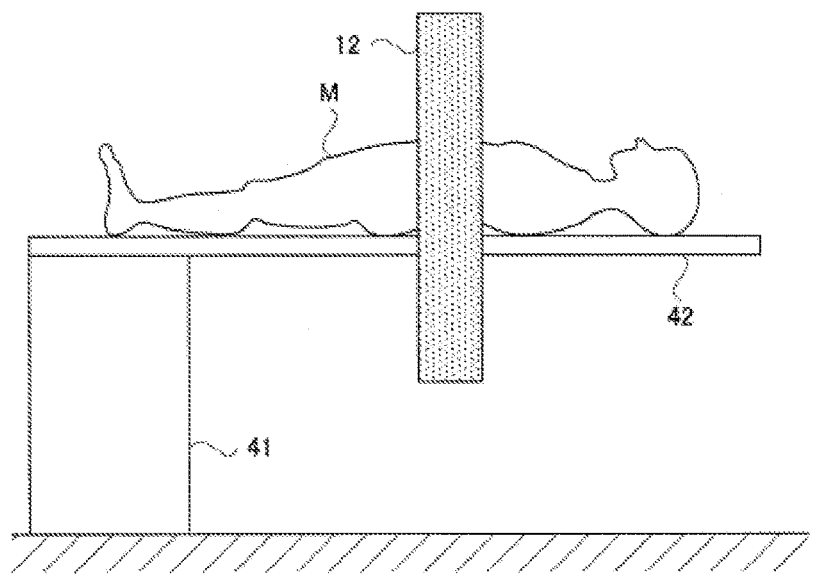
FIG. 15 is a schematic diagram illustrating the operation to transform the detector ring according to Example 1.

FIG. 14 illustrates a state in which the auxiliary unit 12c has been moved to the position of the detector ring 12 after the end of the rotational motion illustrated in FIG. 13. The movement of the auxiliary unit 12c at this moment is performed by the unit slide mechanism 32 as illustrated in FIG. 8. Thus, the auxiliary unit 12c becomes a member included in the detector ring 12, and the C-shaped detector ring 12 changes to an annular shape. FIG. 15 illustrates the apparatus in the state in FIG. 14 from a different viewpoint. FIG. 15 reveals that the patient M is stationary inside the annular-shaped detector ring 12.

As described above, the present invention can provide a radiation tomography apparatus that can generate a functional image with good image quality. In other words, in the configuration of the present invention, the annular-shaped detector ring 12 has the first unit 12a and the second unit 12b that are rotatably movable and the auxiliary unit 12c movable in the central axis direction. The auxiliary unit 12c is moved in the central axis direction relative to the units 12a and 12b, whereby the detector ring 12 forms into a C shape to form a clearance.

However, the support member 15 supporting the auxiliary unit 12c is positioned near this clearance. Hence, in the present invention, the first unit 12a and the second unit 12b are rotatably moved additionally to move the clearance of the detector ring 12 to a position distant from the support member 15. By doing so, the patient M can be introduced from a direction orthogonal to the central axis c of the detector ring 12 without interference from the support member 15. The detector ring 12 is restored to the annular shape in the reverse sequence of the above one with the patient M introduced, whereby annihilation radiation pairs can be detected from all directions to take a tomographic image, and a functional image with higher image quality than that of a conventional configuration can be obtained.

In the present invention, all the members included in the detector ring 12 are supported on the single support member 15. With this configuration, the positional relation among the units 12a, 12b, and 12c included in the detector ring 12 can be reliably fixed. In this regard, in a configuration in which the units 12a, 12b, and 12c are supported on separate support members 15, when the positional relation among the support members 15 changes, the shape of the detector ring 12 also changes. The present invention is free from such an inconvenience.

The present invention is not limited to the configuration described above and can be performed in a modified manner as follows.

Figure 16:
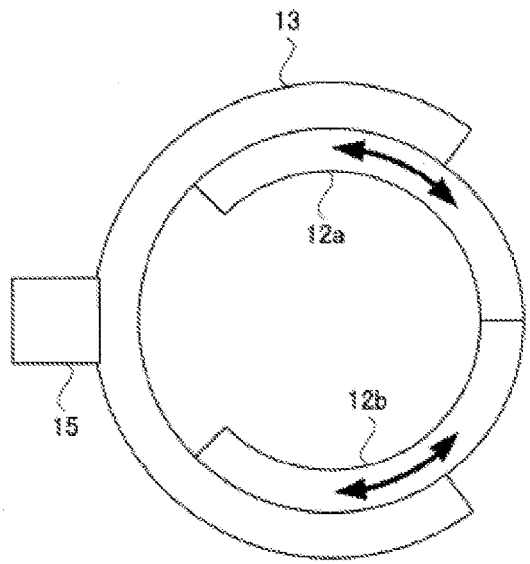
FIG. 16 is a schematic diagram illustrating a modification according to the present invention.
Figure 17:
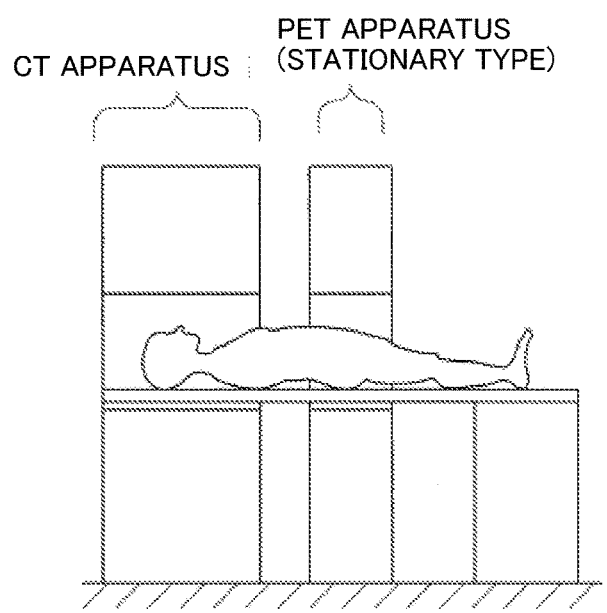
FIG. 17 is a schematic diagram illustrating clearance ET apparatus of a conventional configuration.

(1) Although the guides 13a and 13b supporting the respective units 12a and 12b rotatably move to rotate the respective units 12a and 12b in the configuration described above, the present invention is not limited to this configuration. As illustrated in FIG. 16, the units 12a and 12b themselves can also rotatably move. In this configuration, a C-shaped guide 13 is included, and the units 12a and 12b travel along this guide 13, whereby rotational movement of the units 12a and 12b is performed. The guide 13 is fixed to the support member 15. Consequently, even when the units 12a and 12b rotate, the guide 13 does not move relative to the support member 15.

In other words, the apparatus according to the present modification includes the arc guide 13 supporting the first unit 12a and the second unit 12b. The unit rotation mechanism 33a moves the first unit 12a relative to the guide 13 to perform rotational movement of the first unit 12a, whereas the unit rotation mechanisms 33b moves the second unit 12b relative to the guide 13 to perform rotational movement of the second unit 12b.

The present modification can make the apparatus configuration simpler.

(2) Although the configuration described above divides the detector ring 12 into three, each of which is moved, the present invention is not limited to this configuration; the detector ring 12 may be divided into four or more.

(3) Although the configuration described above is used in combination with the MRI apparatus, the present invention is not limited to this configuration. The present invention can also be used in combination with another apparatus such as a CT apparatus.

(4) Although the mechanisms 31, 32, 33a, and 33b of the present invention are manually operated, the mechanism can also be automatically moved in place of this configuration. In this modification, a controller that controls the mechanisms is provided.

The invention claimed is:

1. A radiation tomography apparatus comprising:
    a detector ring including a first unit including radiation detectors arranged in an arc and detecting radiations, a second unit including the radiation detectors arranged in an arc, and an auxiliary unit including the radiation detectors arranged in an arc, such that the radiation detectors included in the first unit, the second unit, and the auxiliary unit are arranged annularly;
    a support member that supports the detector ring and is provided close to the auxiliary unit among the respective units;
    an auxiliary unit mover that moves the auxiliary unit in a central axis direction of the detector ring relative to the first unit and the second unit;
    a first unit rotator that rotatably moves the first unit about the central axis; and
    a second unit rotator that rotatably moves the second unit about the central axis.

2. The radiation tomography apparatus of claim 1, wherein
    the first unit rotator rotates the first unit and the second unit rotator rotates the second unit to bring the first unit and the second unit close to the support member, so that end parts of the first unit and the second unit, adjacent to each other before the rotations, are separated from each other, and a clearance is generated between the first unit and the second unit such that, through the clearance, a patient is introduced inside the detector ring from a direction orthogonal to the central axis.

3. The radiation tomography apparatus of claim 1, wherein the first unit rotator rotates the first unit and the second unit rotator rotates the second unit to separate the first unit and the second unit from the support member, so that end parts of the first unit and the second unit, adjacent to each other before the rotations, are separated from each other, and a clearance is generated between the first unit and the second unit such that, through the clearance, the auxiliary unit is introduced from a direction in which the central axis extends.

4. The radiation tomography apparatus of claim 1, further comprising:
    a first arc guide fixing the first unit; and
    a second arc guide fixing the second unit, wherein
    the first unit rotator rotates the first guide to perform rotational movement of the first unit, and
    the second unit rotator rotates the second guide to perform rotational movement of the second unit.

5. The radiation tomography apparatus of claim 1, further comprising:
    an arc guide supporting the first unit and the second unit, wherein
    the first unit rotator moves the first unit relative to the guide to perform rotational movement of the first unit, and
    the second unit rotator moves the second unit relative to the guide to perform rotational movement of the second unit.

6. The radiation tomography apparatus of claim 1, further comprising:
    a vehicle moving the detector ring in a direction orthogonal to the central axis.

7. The radiation tomography apparatus of claim 1, further comprising:
    a support member elevator that raises and lowers the support member to raise and lower the detector ring.

8. The radiation tomography apparatus of claim 1 arranged in an MRI apparatus.

9. The radiation tomography apparatus of claim 1 arranged in a CT apparatus.

\* \* \* \* \*